United States Patent
Cho et al.

(10) Patent No.: US 7,873,410 B2
(45) Date of Patent: Jan. 18, 2011

(54) IMPLANTABLE MEDICAL DEVICE WITH ELECTROMECHANICAL DELAY MEASUREMENT FOR LEAD POSITION AND VENTRICULAR

(75) Inventors: Yong K. Cho, Maple Grove, MN (US); Beth J. Geiman-Ferri, Delran, NJ (US); Tommy D. Bennett, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 252 days.

(21) Appl. No.: 11/380,350

(22) Filed: Apr. 26, 2006

(65) Prior Publication Data
US 2007/0255327 A1 Nov. 1, 2007

(51) Int. Cl.
A61B 5/02 (2006.01)
A61N 1/04 (2006.01)

(52) U.S. Cl. .................................. 600/513; 607/28
(58) Field of Classification Search ............... 600/508, 600/513; 607/9, 17, 23, 25, 19, 28
See application file for complete search history.

(56) References Cited

U.S. PATENT DOCUMENTS

| | | | |
|---|---|---|---|
| 5,334,222 A | 8/1994 | Salo et al. | |
| 5,674,256 A | 10/1997 | Carlson | |
| 5,910,120 A | 6/1999 | Kim et al. | |
| 5,944,746 A * | 8/1999 | Kroll | 607/27 |
| 6,195,584 B1 | 2/2001 | Hill et al. | |
| 6,347,249 B1 | 2/2002 | Kim et al. | |
| 6,445,952 B1 | 9/2002 | Manrodt et al. | |
| 6,490,486 B1 * | 12/2002 | Bradley | 607/28 |
| 6,871,088 B2 | 3/2005 | Chinchoy | |
| 2002/0151938 A1 * | 10/2002 | Corbucci | 607/25 |
| 2003/0144703 A1 * | 7/2003 | Yu et al. | 607/17 |
| 2004/0127792 A1 * | 7/2004 | Siejko et al. | 600/439 |
| 2004/0172077 A1 | 9/2004 | Chinchoy | |
| 2005/0004611 A1 | 1/2005 | Edwards et al. | |
| 2005/0027320 A1 * | 2/2005 | Nehls et al. | 607/9 |
| 2005/0038481 A1 * | 2/2005 | Chinchoy et al. | 607/17 |
| 2005/0113897 A1 | 5/2005 | Seifert et al. | |
| 2005/0209648 A1 | 9/2005 | Burnes et al. | |
| 2006/0020294 A1 * | 1/2006 | Brockway et al. | 607/17 |
| 2006/0074453 A1 * | 4/2006 | Kieval et al. | 607/9 |
| 2006/0178586 A1 * | 8/2006 | Dobak, III | 600/508 |

(Continued)

FOREIGN PATENT DOCUMENTS

WO WO 93/20890 10/1993

(Continued)

OTHER PUBLICATIONS

International Search Report, PCT/US2007/066559, Apr. 10, 2007, 7 Pages.

*Primary Examiner*—Carl H Layno
*Assistant Examiner*—Luther G Behringer
(74) *Attorney, Agent, or Firm*—Stephen W. Bauer; Reed A. Duthler

(57) ABSTRACT

The cardiac rhythm management system includes an implantable medical device (IMD) with leads carrying electrodes for sensing cardiac electrical activity, and a physiologic sensor for sensing cardiac mechanical activity. The IMD measures electromechanical delays between electrical activity sensed by the electrodes and mechanical activity sensed by the physiologic sensor. The measured electromechanical delays can be used to detect lead dislodgement and to assess dyssynchrony between two areas of the heart, such as the right ventricle and the left ventricle.

24 Claims, 5 Drawing Sheets

U.S. PATENT DOCUMENTS

2006/0190045 A1 * 8/2006 Marcus et al. .................. 607/17
2006/0276849 A1 * 12/2006 Carlson et al. ................. 607/23
2007/0066913 A1 * 3/2007 Patangay et al. ............ 600/528

FOREIGN PATENT DOCUMENTS

| | | |
|---|---|---|
| WO | WO 99/66984 | 12/1999 |
| WO | 0066219 A | 11/2000 |
| WO | WO 2007/127621 | * 11/2007 |

* cited by examiner

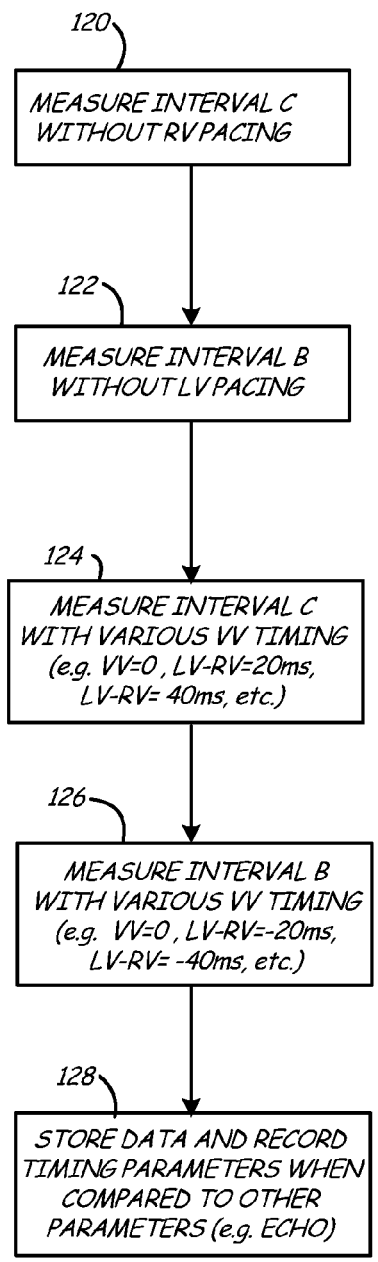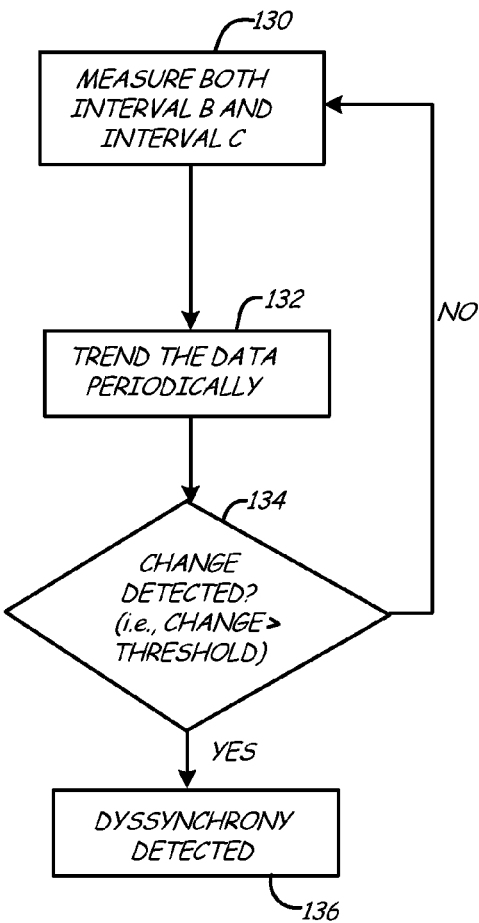
Fig. 5
Fig. 6

IMPLANTABLE MEDICAL DEVICE WITH ELECTROMECHANICAL DELAY MEASUREMENT FOR LEAD POSITION AND VENTRICULAR

BACKGROUND OF THE INVENTION

The present invention relates generally to implantable medical devices (IMDs) and cardiac rhythm management systems. In particular, the present invention relates to measurement of electromechanical delays, which can be used to detect lead displacement or migration of electrical leads, or to assess ventricular dyssynchrony.

IMDs, such as pacemakers, implantable cardioverter defibrillators and implantable hemodynamic monitors, are used to monitor cardiac conditions and deliver therapy when appropriate. The IMDs typically include electrical leads that carry electrodes for pacing, cardioverting, defibrillating, sensing and monitoring functions. The leads may also include a physiologic sensor, such as a pressure sensor, oxygen sensor, temperature sensor, flow sensor, or accelerometer.

Dislodgement or migration of leads can compromise the benefits of cardiac therapy or monitoring by shifting the location of the electrodes (as well as any physiologic sensor carried by the leads). Detection of dislodgement or displacement of leads automatically by an IMD can provide a physician an opportunity to take corrective action to reposition or replace dislodged lead.

Implantable cardiac resynchronization therapy (CRT) systems using bi-ventricular pacing have been introduced to treat patients with heart failure. More than twenty million people worldwide suffer from heart failure, with about two million new cases diagnosed each year. With some patients, heart failure disease affects the synchronous beating action of the left ventricle and right ventricle until the left ventricle cannot pump blood efficiently to supply the body with oxygen and nutrients. These patients tend to tire easily, have a poor quality of life, and can deteriorate rapidly toward the need of a heart transplant or death.

Cardiac resynchronization therapy helps to coordinate the left ventricle and right ventricle of the heart in patients with moderate to severe heart failure. It helps to improve the pumping power of the heart, can make the patients feel better, increase their energy levels, and improve their exercise capacity.

Cardiac resynchronization therapy (CRT) systems typically include a right atrial lead, a right ventricular lead, and a left ventricular lead introduced via the coronary sinus into the coronary venous system to provide stimulation to the left ventricle. Some CRT systems also include a pressure sensor carried by one of the leads to measure pressure in the right ventricle. The measured pressure provides feedback for delivery of CRT pacing.

The CRT system receives sensed signals from the electrodes and provides pacing pulses so that depolarization of the left ventricle is synchronized with depolarization of the right ventricle. By synchronizing the left and right ventricles, stroke volume of the heart can be enhanced. The extent of ventricular dyssynchrony can change over time as a result of physiologic changes, and may require adjustment of timing of the CRT pacing.

BRIEF SUMMARY OF THE INVENTION

An implantable medical device measures time delays between sensed electrical activity and sensed mechanical activity of the heart. The measured time delays can be used to detect sensor movement indicating dislodgement or migration of a lead. It can also be used to provide an assessment of ventricular dyssynchrony, to determine timing parameters for cardiac resynchronization therapy, and to detect dyssynchrony requiring an adjustment of CRT timing parameters.

BRIEF DESCRIPTION OF THE DRAWINGS

FIG. 5 is a block diagram that shows a method of assessing ventricular dyssynchrony with electromechanical delay measurements for use in determining CRT timing parameters.

FIG. 6 is a flow chart showing the use of electromechanical delay measurements for detection of ventricular dyssynchrony.

DETAILED DESCRIPTION

Figure 1:
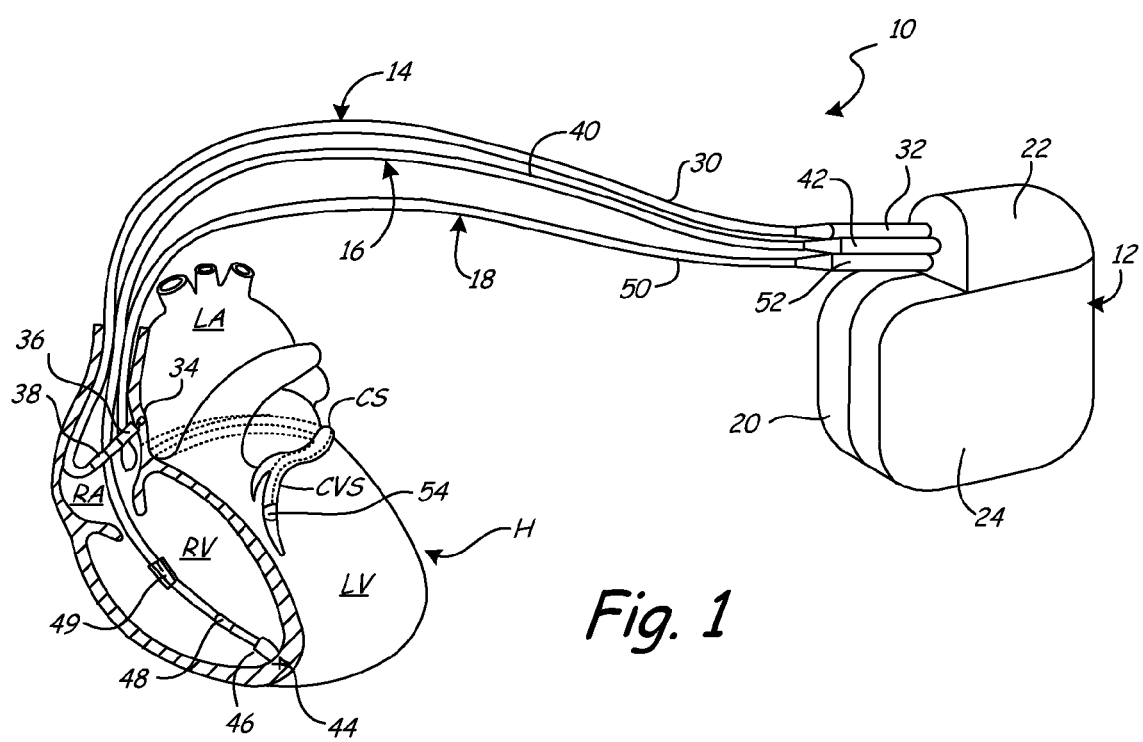
FIG. 1 depicts an example of a cardiac resynchronization therapy (CRT) system in which the present invention may be implemented.

FIG. 1 shows cardiac resynchronization therapy (CRT) system 10, which restores ventricular synchronization in heart H by delivering pacing pulses to one or more chambers of heart H. In FIG. 1, heart H is shown in a partially cutaway view illustrating right atrium RA, left atrium LA, right ventricle RV, left ventricle LV, coronary sinus CS, and coronary venous system CVS.

CRT system 10 includes implantable pulse generator (IPG) 12, right atrial (RA) lead 14, right ventricular (RV) lead 16, and left ventricular (LV) lead 18. As shown in FIG. 1, IPG 12 includes housing or canister 20, header 22 and can electrode 24. The circuitry and power source of IPG 12 are located within housing 20. The circuitry communicates with leads 14, 16, and 18 through electrical connectors within header 22. Can electrode 24 is formed on or is a part of the outer surface of housing 20, and acts as a remote indifferent electrode with respect to one or more of the electrodes carried by leads 14, 16, and 18.

As shown in FIG. 1, RA lead 14 is a bipolar endocardial lead that is passed through a vein into right atrium RA of heart H. RA lead 14 includes lead body 30, connector 32, distal tip attachment mechanism 34, distal tip RA electrode 36, and proximal ring RA electrode 38. Lead body 30 contains a pair of electrically insulated conductors which extend from connector 32 to electrodes 36 and 38. Connector 32 is inserted into a connection bore within header 22 to provide an electrical connection between electrodes 36 and 38 and the circuitry within IPG housing 20. The distal end of RA lead 14 is attached to the wall of right atrium RA by attachment mechanism 34, which may be, for example, a screw or tined fastener.

RV lead 16 is a bipolar endocardial lead that is passed through right atrium RA and into right ventricle RV. RV lead 16 includes lead body 40, connector 42, distal tip attachment mechanism 44, distal tip RV electrode 46, proximal ring RV electrode 48, and pressure sensor 49, (typically placed in the right ventricular outflow tract RVOT). Lead body 40 of RV lead 16 contains a pair of electrically insulated conductors which extend from connector 42 to electrodes 46 and 48 and pressure sensor 49. Connector 42 is at the proximal end of RV lead 16, and is inserted into a connection bore of header 22 to provide an electrical connection between the circuitry within housing 20 and electrodes 46 and 48 and pressure sensor 49. Distal tip electrode 46 is placed in contact with the apex of right ventricle RV and is fixed in place by attachment mechanism 44.

LV lead 18 includes lead body 50, connector 52 and LV electrode 54. Lead body 50 contains an electrically insulated conductor which extends from connector 52 at the proximal end of lead 18 to electrode 54 at the distal end of lead 18. Connector 52 is inserted into a bore within header 22 to provide electrical connection between LV electrode 54 and the circuitry within housing 20.

In this embodiment, LV lead 18 is passed through right atrium RA into coronary sinus CS and then into a cardiac vein of coronary venous system CVS. LV lead 18 is shown as a unipolar lead, so that sensing of electrogram (EGM) signals and application of pacing pulses through LV electrode 54 is performed with respect to one of the other electrodes 24, 36, 38, 46, or 48 of CRT system 10. Alternatively, LV lead 18 can carry more than one electrode and perform as a bipolar lead.

LV lead 18 is configured so that LV electrode 54 will lodge within a cardiac vein and will remain in position despite having no attachment mechanism comparable to attachment mechanism 34 of RA lead 14 or attachment mechanism 44 of RV lead 16. LV electrode 54 is positioned within the cardiac vein during implantation to achieve desired synchronous pacing performance.

CRT system 10 makes use of the ability to sense both electrical activity and mechanical activity to detect lead dislodgement, and to assess ventricular dyssynchrony. CRT system 10 uses sensed electrical activity as a trigger for measuring a time delay between electrical activity and a corresponding mechanical activity.

Figure 2:
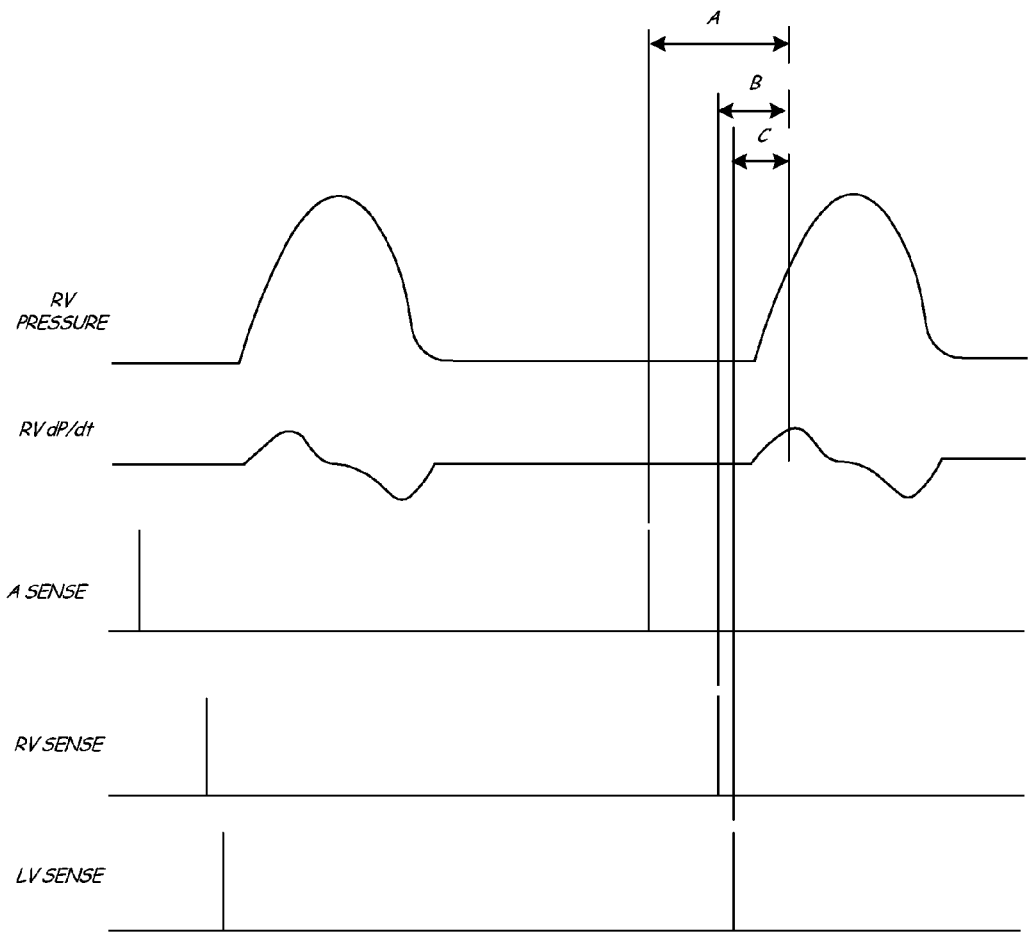
FIG. 2 shows waveforms representing sensed cardiac mechanical and electrical activity.

FIG. 2 shows waveforms illustrating one example of sensed electrical and mechanical activity. RV Pressure waveform represents right ventricular sensed by pressure sensor 49. The RV dP/dt waveform represents the first derivative of the RV Pressure waveform. The A Sense waveform represents sensed P-waves (atrial depolarizations) sensed by RA electrodes 36 and 38. The RV Sense waveform represents R-waves (ventricular depolarizations) sensed by RV electrodes 46 and 48. The LV Sense waveform represents R-waves sensed by LV electrode 54.

FIG. 2 also illustrates three time intervals A-C based upon delays between sensed electrical and mechanical activity. Interval A represents the time from an A Sense event to maximum change in pressure (RV dP/dt max). Interval B represents the time from an RV Sense event to RV dP/dt max. Interval C represents the time from an LV Sense event to RV dP/dt max.

Electromechanical time delay measurements, such as intervals A-C, representing the time from an electrical event sensed by an electrical sensor to a mechanical event sensed by a mechanical sensor can be used to estimate distance between the electrical sensor, and the mechanical sensor. Pathophysiologic electromechanical remodeling does not take place in a short time period. By sampling the electromechanical delay frequently, a sudden change in one or more of intervals A-C may mean a change in lead positions representing a lead dislodgement or migration.

In CRT system 10, intervals A-C can be measured using the right atrial electrical sensor (formed by electrodes 36 and 38), the right ventricular electrical sensor (formed by electrodes 46 and 48), or the left ventricular sensor (formed by electrode 54) as the trigger for measuring time delay. The electromechanical delay measurement will depend upon the physical distance of the RA, RV, or LV sensor with respect to pressure sensor 49. The measurement can be triggered using either sensed or paced activity. One interval, or a combination of intervals A-C, can be used by IPG 12 to assess lead position changes. When there is a sudden change in one of the delay measurements, other measurements, using the other electrical sensors, can be evaluated to see whether the change occurred due to a movement of pressure sensor 49, or whether it occurred due to a movement of one of the electrodes. If only one of the intervals changed, this indicates movement of an electrode. However, if intervals triggered by more than one electrodes with respect to pressure sensor 49 have changed, the changes are likely due to a movement of pressure sensor 49.

Electromechanical delay measurements can also be used to assess the dyssynchrony between two areas of the heart. This is particularly useful in CRT therapy to assess dyssynchrony between right ventricle RV and left ventricle LV.

Using measured intervals A-C at different AV or VV timing intervals, the degree of ventricular dyssynchrony can be determined. The electromechanical delay indicates the time between electrical activation at a particular site to mechanical activation at pressure sensor 49. This information can be used to adjust AV or VV timing parameters in order to synchronize the right and left ventricles during initialization of CRT system 10. By continuing to monitor intervals B and C over time, physiological changes resulting in dyssynchrony can be detected, and used to guide adjustment of AV or VV timing parameters. In addition, the delay measurements can be used to assess effective electrical stimulation levels, and the loss of effective stimulation when no changes in electromechanical delays are detected despite changes in AV or VV timing from one of the electrical sensor locations.

Intervals A-C are only one example of electromechanical delays that can be used. Rather than RV dP/dt max, the marker derived from the mechanical signal (RV Pressure) can be maximum pressure (P max), minimum pressure (P min) or minimum first derivative of pressure (dP/dt min). In addition, pressure can be sensed in locations other than the RVOT, (e.g. the coronary sinus vein).

Other types of mechanical activity sensors can also be used. For example, an accelerometer can be used to provide a marker representing peak endocardial acceleration, which is associated with valve opening and closing. The accelerometer may, for example, be carried on LV lead 18 and positioned in the coronary sinus (CS) vein.

In another embodiment, the mechanical activity is a physical dimension or volume measurement representative of changing dimension or volume of a chamber of the heart. The measurement may be, for example, intracardiac impedance (Z), and the marker may be Z max or dZ/dt max.

Figure 3:
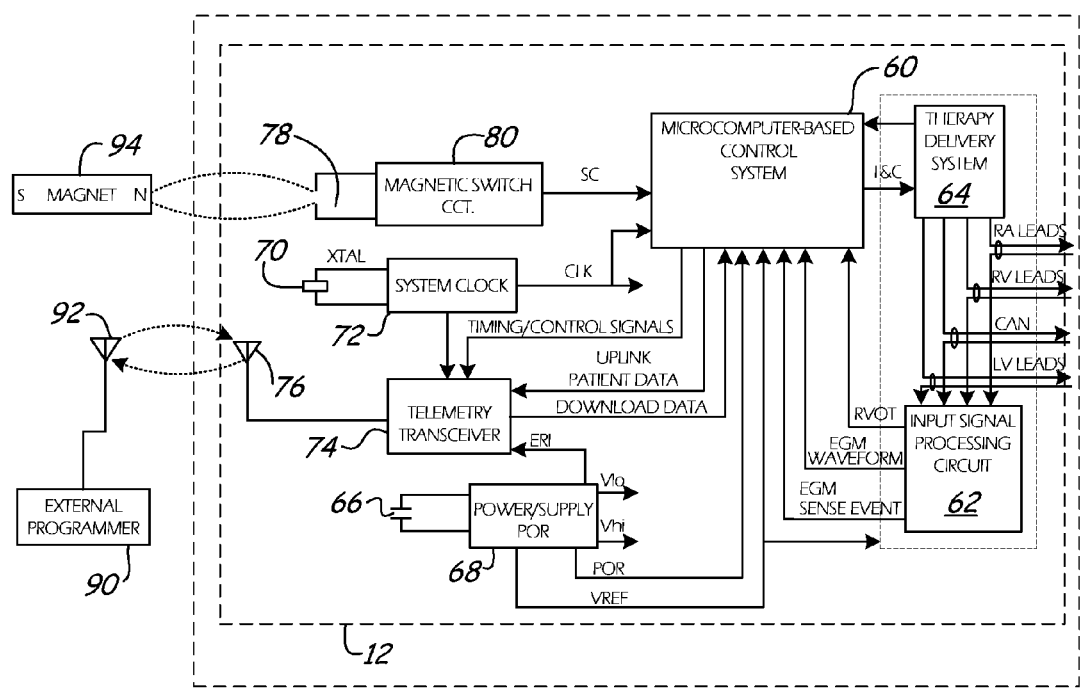
FIG. 3 is a block diagram of an implantable pulse generator used in the CRT system of FIG. 1.

FIG. 3 is an electrical block diagram of IPG 12 that provides delivery of resynchronization therapy through leads 14, 16 and 18 shown in FIG. 1. As shown in FIG. 3, IPG 12 includes microcomputer-based control system 60, input signal processing circuit 62, therapy delivery system 64, battery 66, power supply/power on reset (POR) 68, crystal oscillator 70, system clock 72, telemetry transceiver 74, antenna 76, switch 78, and magnetic switch circuit 80. Also shown in FIG. 3 are external programmer 90 and antenna 92 (which communicate with IPG 12 through antenna 76 and transceiver 74), and magnet 94 (which interacts with pacemaker 12 through switch 78 and magnetic switch circuit 80).

Control system 60 controls the functions of IPG 12 by executing firmware and program software algorithms stored in associated RAM and ROM. Control system 60 may also include additional circuitry including a watchdog circuit, a DMA controller, a block mover/reader, a CRC calculator, and other specific logic circuitry coupled together by an on-chip data bus, address bus, power, clock, and control signal lines. Control and timing functions can also be accomplished in whole or in part with dedicated circuit hardware or state machine logic rather than a programmed microcomputer.

Input signal processing circuit 62 receives signals from RA lead 14, RV lead 16, LV lead 18 and can electrode 24. The outputs of input signal processing circuit 62 include digitized EGM waveforms, P-wave and R-wave sensed event signals, and pressure signals derived from leads 14, 16, and 18.

Input signal processing circuit 62 includes a plurality of channels for sensing and processing cardiac signals from electrodes carried by leads 14, 16, and 18. Each channel typically includes a sense amplifier circuit for detecting specific cardiac events and an EGM amplifier circuit for providing the EGM waveform signal to control system 60, where the EGM waveform is sampled, digitized and stored.

Therapy delivery system 64 delivers cardiac pacing pulses to leads 14, 16, and 18 to control the patient's heart rhythm and to resynchronize heart chamber activation. Delivery of the cardiac pacing pulses by therapy delivery system 64 is under the control of control system 60. Delivery of pacing pulses to two or more heart chambers is controlled in part by the selection of programmable pacing intervals, which can include atrial-atrial (AA), atrial-ventricular (AV) and ventricular-ventricular (VV) intervals.

Therapy delivery system 64 can optionally be configured to include circuitry for delivering cardioversion/defibrillation therapy in addition to cardiac pacing pulses for controlling a patient's heart rhythm. Accordingly, leads 14, 16, and 18 can additionally include high voltage cardioversion or defibrillation shock electrodes.

Electrical energy for IPG 12 is supplied from battery 66 through power supply/power on reset (POR) circuit 68. This includes power to operate the circuitry controlling operation of IPG 12, as well as electrical stimulation energy for delivery to heart H, and power for telemetry signal transmissions. Power supply/POR circuit 68 provides low voltage power Vlo, power on reset (POR) signal, reference voltage VREF, elective replacement indicator signal ERI and high voltage power Vhi (if CRT system 10 also has cardioversion/defibrillation capabilities).

Clock signals for operation of the digital logic within IPG 12 are provided by crystal oscillator 70 and system clock 72. Uplink and downlink telemetry capabilities are provided through telemetry transceiver 74 and antenna 76. External programmer 90 can receive stored EGM data, as well as realtime generated physiologic data and nonphysiologic data from control system 60. In addition, programming data can be supplied from external programmer 90 to control system 60.

Magnetic field sensitive switch 78 and magnetic switch circuit 80, issue a switch closed (SC) signal to control system 60 when magnet 94 is positioned over subcutaneously implanted IPG 12. Magnet 94 may be used by the patient to prompt control system 60 to deliver therapy or to store physiologic data. Alternatively, the long-range telemetry without a magnet can be used to provide a prompt to control system 60.

Figure 4:
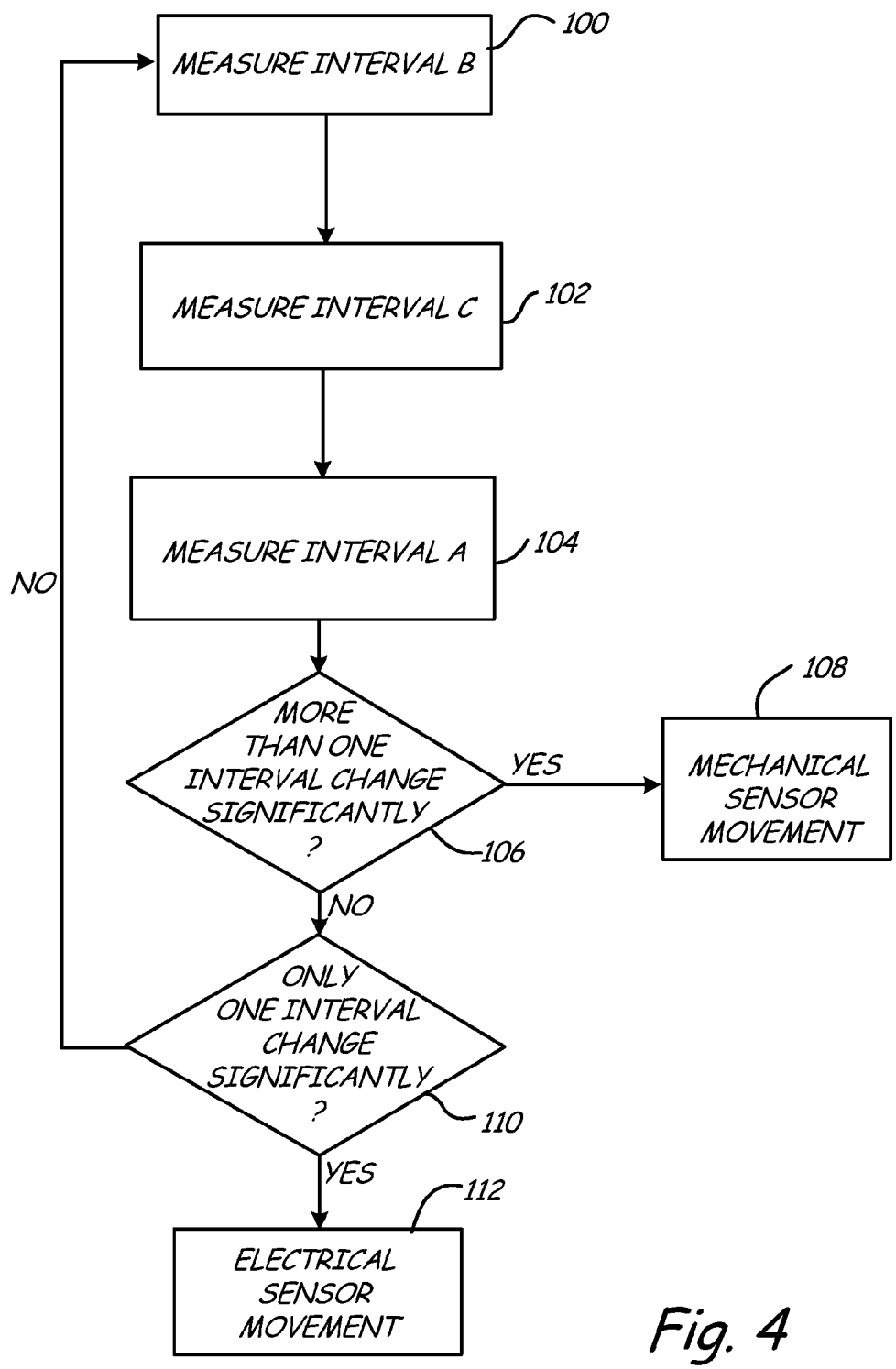
FIG. 4 is a flow chart that shows a method of detecting sensor movement with electromechanical delay measurements.

FIG. 4 is a block diagram showing the use of electromechanical delay measurements to measure relative distance between RV, LV, and RA electrodes and pressure sensor 49 to detect lead position features. As shown in FIG. 4, interval B is measured using the RV Sense signal from electrodes 46 and 48 as the trigger to start the time delay measurement (step 100). Interval B represents the time delay from an RV Sense event (either a sensed R-wave or an RV pacing pulse) to the maximum dp/dt from sensor 49.

At step 102, interval C time delay measurement is made using an LV Sense event from electrode 54 as the trigger. Next, an interval A measurement is made using an A Sense event (or a sensed P-wave pacing pulse) at RA electrodes 36 and 38 as the trigger (step 104).

Control system 60 then compares each of the measured electromechanical delays to a corresponding previous measurement (step 106). If two or more of the measurements differ significantly (e.g. by greater than an allowed error range) from a corresponding earlier measurement, control system 60 determines that pressure sensor 49 has moved (step 108). This likely represents a dislodgement of RV lead 16.

Control system 60 also determines if only one of the electromechanical delay measurements differed significantly from its corresponding previous measurement (step 110). If none of the delay measurements differed significantly from the previous measurements, control system 60 returns to step 100 to repeat the measurement process at a scheduled future time. If one of the delay measurements departed significantly from its previous measurement, control system 60 identifies the particular electrical sensor that triggered the measurement as having moved. Upon recognition of a change indicating a dislodgement or migration of RA, RV or LV electrodes (or of pressure sensor 49), an annunciating response is produced. This response can be a warning sound that indicates to the patient that the patient should visit a physician. Alternatively, the annunciating response can be in the form of uplink patient data supplied through telemetry transceiver 74 to external programmer 90, or automatic long-range telemetry communication can deliver the communicating response to a home monitor which, in turn, transmits data to a central server.

Although FIG. 4 shows a process in which electromechanical delays (intervals A-C) are measured using RA, RV, and LV triggering during each measurement cycle, other alternatives are possible. For example, one of the electromechanical delays can be measured routinely, and the other delay measurements can be made only when there is a change detected in the one delay measurement that is made routinely.

Electromechanical delay measurement can also be used to assess dyssynchrony between two areas of the heart, such as the right and left ventricles. FIG. 5 shows a flow diagram showing the use of electromechanical delay measurements in determining timing parameters to be used for CRT therapy.

In FIG. 5, interval C (LV sense to dP/dt max electromechanical delay) is measured without right ventricular (RV) pacing taking place (step 120). Next, interval B (RV Sense to dP/dt max electromechanical delay) is measured without left ventricular (LV) pacing (step 122).

Using LV electrical activity as a trigger, interval C is then measured with various VV timing intervals between RV and LV pacing. In the example shown, the intervals may be VV=0, LV-RV=20 ms, LV-RV=40 ms, and so on, at increments of 20 milliseconds each.

Next, interval B is measured using RV electrical activity as the trigger (step 126). As in step 124, various VV timing intervals are used, such as VV=0, LV-RV=-20 ms, LV-RV=-40 ms, etc.

The electromechanical delay measurements are stored by control system 60. The stored delay measurements are used together with other measured parameters to determine base line or optimal timing parameters to be used for CRT therapy (step 128).

FIG. 6 is a flow diagram showing the use of electromechanical delay measurements over time to detect ventricular dyssynchrony. Periodically, both interval B and interval C are measured (step 130). The measurements are stored, and the data is analyzed periodically (step 132). A determination is made whether a change in the data has occurred which exceeds a threshold value (step 134). If not, the periodic measurement of electromechanical delays continues. If a change greater than a threshold has been detected, an indication that dyssynchrony has been detected is provided by control system 60 (step 136).

The presence of a mechanical physiologic sensor (such as a pressure sensor, an accelerometer, or an intracardiac impedance sensor) provides additional functionality when used in conjunction with electrical sensors. Electromechanical delay measurements can be made that represent a delay between a sensed electrical event and a subsequent related mechanical activity of the heart. The electromechanical delay measurements provide useful information for detecting dislodgement or migration of sensors or leads, determining timing parameters for CRT therapy, and detection of ventricular dyssynchrony as a result of physiological changes over time.

Although the present invention has been described with reference to preferred embodiments, workers skilled in the art will recognize that changes may be made in form and detail without departing from the spirit and scope of the invention.

The invention clamied is:

1. An implantable medical device (IMD) comprising:
   a plurality of electrical sensors responsive to electrical activity of a heart; and
   producing signals indicative thereof;
   a physiologic sensor responsive to mechanical activity of the heart and producing signals indicative thereof; and
   signal processing circuitry responsive to the signals from the mechanical and electrical sensors and deriving a time delay measurement for each electrical sensor with respect to the physiologic sensor.

2. The IMD of claim 1, wherein the signal processing circuitry comprises:
   means for determining dislodgement of one of the sensors based upon a change in at least one of the time delay measurements.

3. The IMD of claim 1, wherein the signal processing circuitry comprises:
   means for determining ventricular dyssynchrony based upon values of the time delay measurements.

4. The IMD of claim 1, wherein the physiologic sensor comprises one of a pressure sensor, an accelerometer and an impedance sensor.

5. An implantable medical device (IMD) comprising:
   electrodes usable different heart chambers, responsive to electrical activity and producing signals indicative thereof;
   a physiologic sensor responsive to mechanical activity associated with one of the chambers and producing signals indicative thereof; and
   circuitry responsive to the signals from the electrodes and the physiologic sensor, and producing an output based upon electromechanical delays between electrical activity sensed by the electrodes and the mechanical activity sensed by the physiologic sensor.

6. The IMD of claim 5, wherein the output is indicative of dislodgement of a sensor.

7. The IMD of claim 5, further comprising:
   means for providing right ventricular (RV) pacing and left ventricular (LV) pacing; and
   means for defining VV timing between RV pacing and LV pacing; and
   wherein the output is indicative of the VV timing for cardiac resynchronization therapy.

8. The IMD of claim 5, wherein output is indicative of a detected ventricular dyssynchrony.

9. The IMD of claim 5, wherein the physiologic sensor comprises one of a pressure sensor, an accelerometer, and an impedance sensor.

10. An implantable medical device (IMD) comprising:
    a right atrial (RA) lead including an RA electrode producing an RA Sense signal;
    a right ventricular (RV) lead including an RV electrode for producing an RV Sense signal;
    a left ventricular (LV) lead including an LV electrode producing an LV Sense signal;
    a sensor producing a signal representative of cardiac mechanical activity; and
    means for deriving a first electromechanical delay measurement based on the RA Sense signal and the mechanical signal, a second electromechanical delay measurement based on the RV Sense signal and the mechanical signal, and a third electromechanical delay measurement based on the LV Sense signal and the mechanical signal.

11. The IMD of claim 10 and further comprising:
    means for providing an output indicating a dislodgement of one of the electrodes based upon a change in at least on of the delay measurments.

12. The IMD of claim 10, further comprising:
    means for providing right ventricular (RV) pacing and left ventricular (LV) pacing;
    means for defining VV timing intervals between RV pacing and LV pacing; and
    means for measuring the second delay measurement without LV pacing and with LV pacing at various VV timing intervals and
    means for measuring the third delay measurement without RV pacing and with RV pacing at various VV timing intervals.

13. The IMD of claim 12, further comprising:
    means for determining VV timing intervals; and
    means for providing CRT pacing using the VV timing intervals based on the second delay and third delay measurements.

14. The IMD of claim 10, wherein the sensor comprises one of a pressure sensor, an accelerometer, and an impedance sensor.

15. A method of operating a cardiac rhythm management system comprising:
    measuring an electromechanical delay representing a time delay from a first sensed cardiac electrical event to occurrence of a mechanical activity marker using a first electrical sensor and a sensor responsive to mechanical activity;
    measuring an electromechanical delay representing a time delay from a second sensed cardiac electrical event to occurrence of the mechanical activity marker using a second electrical sensor; and
    providing an output as a function of the measured electromechanical delays.

16. The method of claim 15, wherein the output is indicative of dislodgement of a sensor.

17. The method of claim 15, further comprising:
    providing RV pacing and LV pacing;
    defining VV timing between RV pacing and LV pacing; and
    wherein the output is indicative of the VV timing for cardiac resynchronization.

18. The method of claim 15, wherein the output is indicative of a detected ventricular dyssynchrony.

19. The method of claim 15, wherein the mechanical activity marker is based upon a ventricular pressure.

20. The method of claim 19, wherein the mechanical activity marker is representative of one of maximum pressure, minimum pressure, maximum first derivative of pressure as a function of time, and minimum first derivative of pressure as a function of time.

21. The method of claim 15, wherein the mechanical activity marker is representative of peak endocardial acceleration.

22. The method of claim 15, wherein the mechanical activity marker is representative of intracardiac impedance.

23. The method of claim 15, wherein the mechanical activity marker is a function of heart size.

24. The method of claim 15, wherein the mechanical activity marker is a function of heart volume.

* * * * *